United States Patent
Ida

(10) Patent No.: US 10,966,592 B2
(45) Date of Patent: Apr. 6, 2021

(54) 3D ENDOSCOPE APPARATUS AND 3D VIDEO PROCESSING APPARATUS

(71) Applicant: Olympus Corporation, Hachioji (JP)

(72) Inventor: Takayuki Ida, Machida (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

(21) Appl. No.: 16/682,071

(22) Filed: Nov. 13, 2019

(65) Prior Publication Data

US 2020/0077869 A1   Mar. 12, 2020

Related U.S. Application Data

(63) Continuation of application No. PCT/JP2018/014811, filed on Apr. 6, 2018.

(30) Foreign Application Priority Data

May 19, 2017   (JP) .............................. JP2017-099552

(51) Int. Cl.
*A61B 1/05*   (2006.01)
*A61B 1/00*   (2006.01)
(Continued)

(52) U.S. Cl.
CPC ............ *A61B 1/00009* (2013.01); *A61B 1/06* (2013.01); *G06T 7/0012* (2013.01); *G06T 7/11* (2017.01);
(Continued)

(58) Field of Classification Search
CPC ....... A61B 1/00009; A61B 1/06; A61B 1/051; A61B 1/127; G06T 7/11; G06T 7/0012;
(Continued)

(56) References Cited

U.S. PATENT DOCUMENTS

| 5,860,912 A * | 1/1999 | Chiba ................ A61B 1/00193 600/111 |
| 2006/0173358 A1 * | 8/2006 | Xie ..................... A61B 1/00009 600/476 |

(Continued)

FOREIGN PATENT DOCUMENTS

| JP | H8-029701 | 2/1996 |
| JP | H11-318909 | 5/1998 |

(Continued)

OTHER PUBLICATIONS

International Search Report and Written Opinion from corresponding International Application No. PCT/JP2017/014811, dated May 15, 2018.

*Primary Examiner* — Howard D Brown, Jr.
(74) *Attorney, Agent, or Firm* — Oliff PLC

(57) ABSTRACT

A three-dimensional endoscope comprises a video signal input portion to which a first video signal is obtained by a first imaging system and a second video signal is obtained by a second imaging system are inputted. A video signal identification portion that identifies a two-dimensional video signal and a three-dimensional video signal are obtained from the video signal input portion. An image condition detection portion that when the video signal identification portion has detected the two-dimensional video signal, analyzes a display area of a two-dimensional image to detect a foggy region. An image combining portion that, when the image condition detection portion has detected a foggy region in a video of at least one of the first imaging system and the second imaging system, combines both of the first video signal and the second video signal to generate a composite image in which fogginess of the foggy region being eliminated.

16 Claims, 11 Drawing Sheets

(51) Int. Cl.
*G06T 7/11* (2017.01)
*A61B 1/06* (2006.01)
*G06T 7/00* (2017.01)
*G06T 19/00* (2011.01)

(52) U.S. Cl.
CPC ............ *G06T 19/003* (2013.01); *A61B 1/051* (2013.01); *G06T 2200/04* (2013.01); *G06T 2207/10021* (2013.01)

(58) Field of Classification Search
CPC ............... G06T 19/003; G06T 2200/04; G06T 2207/10021; G06T 2207/10068; G06T 2207/30004; G06T 5/005; G06T 5/50; G02B 23/2415
See application file for complete search history.

(56) References Cited

U.S. PATENT DOCUMENTS

| | | | |
|---|---|---|---|
| 2007/0008575 A1 | 1/2007 | Yu et al. | |
| 2014/0163359 A1* | 6/2014 | Sholev | A61B 1/04 600/424 |
| 2014/0350338 A1* | 11/2014 | Tanaka | A61B 1/00193 600/111 |
| 2015/0272694 A1* | 10/2015 | Charles | A61B 90/37 600/202 |
| 2016/0235486 A1* | 8/2016 | Larkin | A61B 1/00154 |
| 2016/0261846 A1* | 9/2016 | Kasumi | A61B 1/00009 |
| 2019/0290110 A1* | 9/2019 | Uchimura | A61B 90/361 |
| 2020/0054243 A1* | 2/2020 | Palushi | A61B 1/04 |
| 2020/0060537 A1* | 2/2020 | Rephaeli | A61B 1/002 |

FOREIGN PATENT DOCUMENTS

| | | |
|---|---|---|
| JP | 2006-352876 | 12/2006 |
| JP | 2011-036582 | 2/2011 |
| JP | 2013-094593 | 5/2013 |
| JP | 2016-158886 | 9/2015 |
| JP | 2015-226216 | 12/2015 |
| WO | 20140136140 | 9/2014 |
| WO | 20150083451 | 8/2015 |

\* cited by examiner

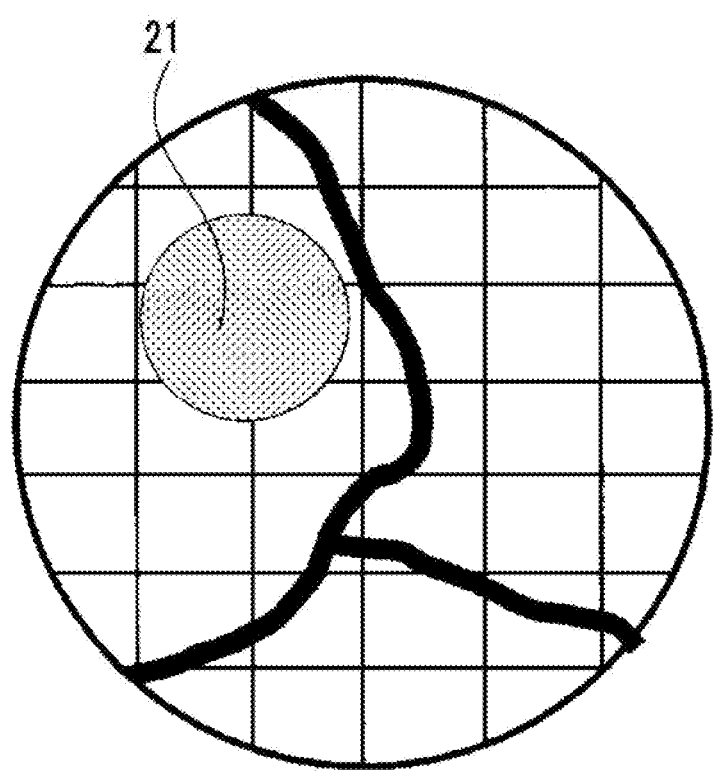

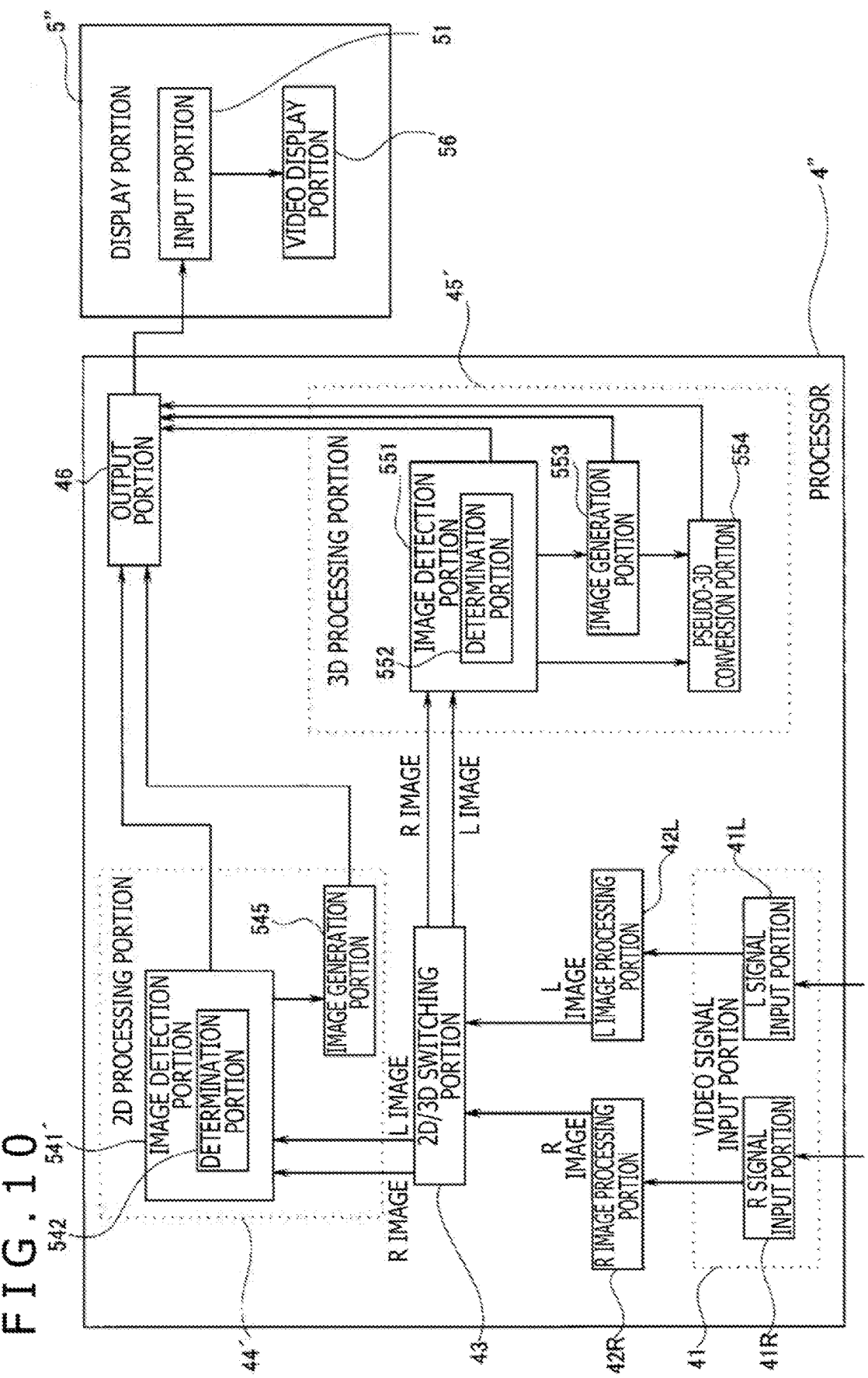

ated to a 3D endoscope apparatus and a 3D video processing apparatus, and in particular, to a 3D endoscope apparatus and a 3D video processing apparatus that allow a switch between two-dimensional (2D) images and 3D images and output the 2D images or 3D images that was selected accordingly.

3D ENDOSCOPE APPARATUS AND 3D VIDEO PROCESSING APPARATUS

CROSS-REFERENCE TO RELATED APPLICATIONS

This application is a continuation application of PCT Application No. PCT/JP2018/014811 filed on Apr. 6, 2018, which in turn claim priority to the Japanese Patent Application No. 2017-99552 filed on May 19, 2017 in Japan which is hereby incorporated by reference in its entirety.

TECHNICAL FIELD

Embodiments of the disclosed technology relate to a three-dimensional (3D) endoscope apparatus and a 3D video processing apparatus, and in particular, to a 3D endoscope apparatus and a 3D video processing apparatus that allow a switch between two-dimensional (2D) images and 3D images and output the 2D images or 3D images that was selected accordingly.

DESCRIPTION OF THE RELATED ART

Endoscope apparatuses have been widely used in the medical field for observing organs in a body cavity, for a curative treatment using a treatment instrument, for an operation under observation using an endoscope, and so on. In a common endoscope apparatus, an imaging signal of a subject obtained by an electronic endoscope having an imaging device, such as a charge-coupled device (CCD) or the like, installed at a distal end of an insertion portion is transferred to a processor, and is subjected to image processing therein. An endoscope image obtained as a result of the image processing is outputted from the processor to an endoscope monitor, and is displayed thereon.

An ordinary endoscope apparatus images an area to be observed using one imaging device, and obtains a 2D endoscope image. Meanwhile, a 3D electronic endoscope including two imaging devices is sometimes used when, for example, an operation is performed. That is, a 3D endoscope apparatus has been developed which allows 3D endoscope images to be taken by obtaining a displacement between images caused by a difference between the positions of the two imaging devices, i.e., a parallax. These images are independently presented to two eyes of a human to have a three-dimensional sense. When such a 3D endoscope apparatus is used, 3D endoscope images that have a three-dimensional sense of depth can be obtained, which may make it easier for an operator to perform an operation or the like as disclosed, for example, in a Japanese Patent Application-JP 2015-226216A.

When a treatment of an organ in a body cavity, such as a laser surgical removal, is performed, a water vapor, a smoke, and so on may be generated during the treatment. If this happens, fogs may occur on, or stains may be attached to objective lenses installed at a distal end of an insertion portion of the electronic endoscope, and this in turn may result in unclear portions of endoscope images, making it difficult to view a whole operative field. In such a situation, in the case of an existing 3D endoscope apparatus, an electronic endoscope is once taken out of the body cavity and is cleaned or heated to remove the fogs or stains, and is again returned into the body cavity to restart the operation. That is, because some time is required to clean the objective lenses, the progress of a manipulation is delayed.

BRIEF SUMMARY OF EMBODIMENTS

One aspect of the disclosed technology is directed to a three-dimensional endoscope apparatus. The three-dimensional endoscope comprises a video signal input portion to which a first video signal is obtained by a first imaging system and a second video signal is obtained by a second imaging system are inputted. A video signal identification portion that identifies a two-dimensional video signal and a three-dimensional video signal are obtained from the video signal input portion. An image condition detection portion that, when the video signal identification portion has detected the two-dimensional video signal, analyzes a display area of a two-dimensional image to detect a foggy region therein. An image combining portion that, when the image condition detection portion has detected a foggy region in a video of at least one of the first imaging system and the second imaging system, combines both of the first video signal and the second video signal to generate a composite image in which fogginess of the foggy region being eliminated.

Another aspect of the disclosed technology is directed to a three-dimensional endoscope apparatus. Three-dimensional endoscope comprises a video signal input portion to which a first video signal is obtained by a first imaging system and a second video signal is obtained by a second imaging system are inputted. An image condition detection portion that analyzes a display area of a first image in the first video signal and/or a display area of a second image in the second video signal to detect a foggy region therein. An image combining portion that, when the image condition detection portion has detected a foggy region in a video of at least one of the first imaging system and the second imaging system, combines both of the first video signal and the second video signal to generate a composite image in which fogginess of the foggy region being reduced or eliminated. A pseudo-three-dimensional conversion portion that simulatively converts, to a three-dimensional video signal, a video signal without a foggy region obtained from one of the first imaging system and the second imaging system or the composite image generated by the image combining portion. A display portion that displays the three-dimensional video signal and a two-dimensional video signal formed by one of the first video signal, the second video signal, and the composite image.

A further aspect of the disclosed technology is directed to a three-dimensional video processing apparatus used in an endoscope system. The endoscope system comprises an endoscope having an elongated insertion portion and an operation portion being attached to one another. A lighting device, a display device and the three three-dimensional video processing apparatus all of which being attached to the endoscope to construct an image of a treatment target during operation. The three-dimensional video processing apparatus includes a video signal input portion to which a first video signal being obtained by a first imaging system and a second video signal being obtained by a second imaging system are inputted. An image condition detection portion that analyzes a display area of a first image in the first video signal and/or a display area of a second image in the second video signal to detect a foggy region therein. An image combining portion that, when the image condition detection portion has detected foggy regions in videos of both the first imaging system and the second imaging system, combines the first video signal and the second video signal to generate a composite image in which fogginess of the foggy regions being eliminated. An output portion that outputs a two-dimensional video signal formed by one of the first video signal, the second video signal, and the composite image.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 3C is a further diagram for explaining an example of an image including a fog.

FIG. 10 is a block diagram for explaining an example structure of a processor according to a third embodiment of the disclosed technology.

DETAILED DESCRIPTION OF THE EMBODIMENTS

Figure 1:
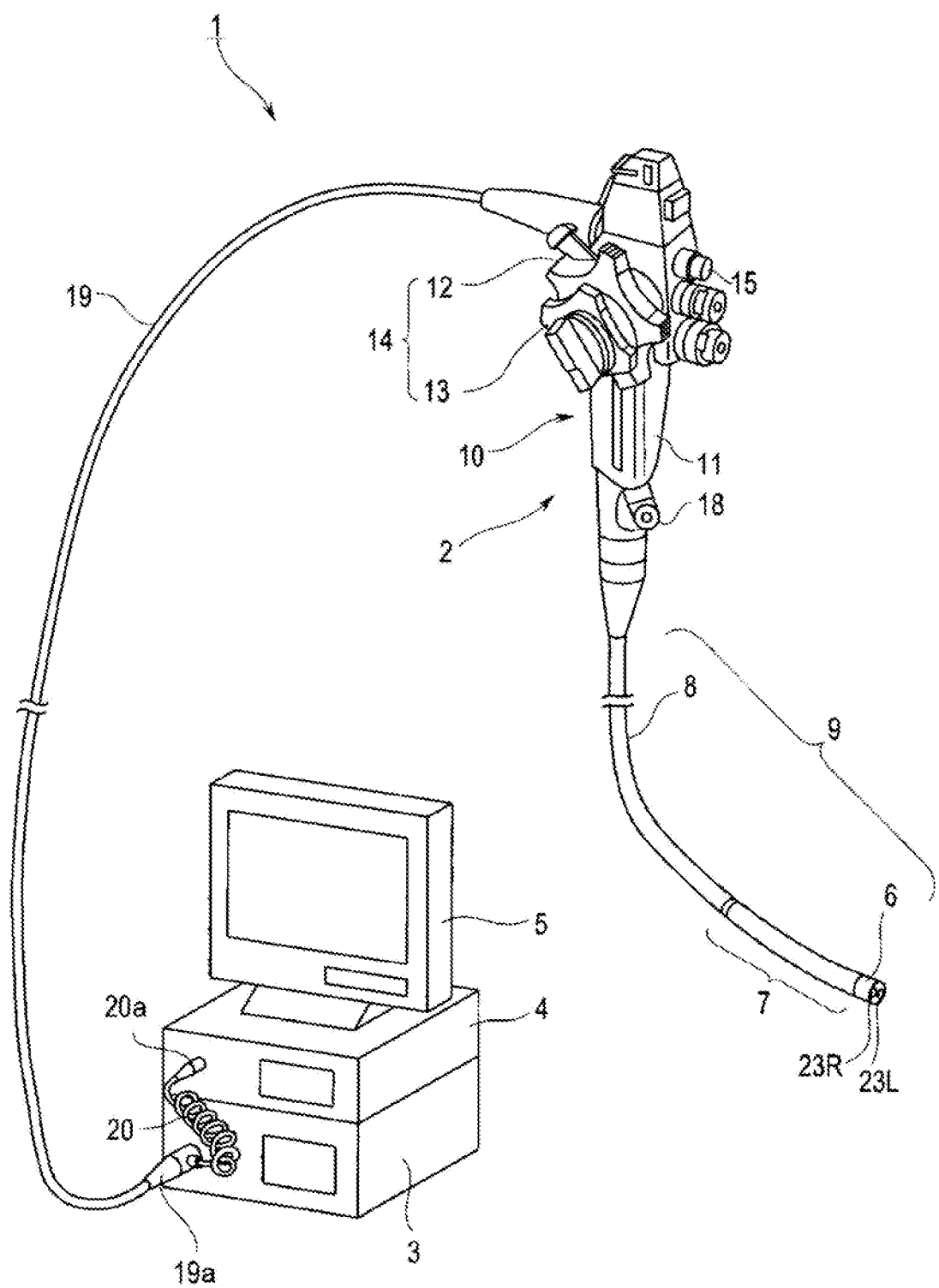
FIG. 1 is a perspective view illustrating an example of the overall structure of an endoscope system including a 3D endoscope apparatus according to an embodiment of the disclosed technology.

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

A 3D endoscope apparatus according to one aspect of the disclosed technology includes: a video signal input portion to which a first video signal obtained by a first imaging system and a second video signal obtained by a second imaging system are inputted; a 2D/3D identification portion that identifies a 2D video signal and a 3D video signal obtained from the video signal input portion; and an image condition detection portion that, when the 2D/3D identification portion has detected the 2D video signal, analyzes a display area of a 2D image to detect a foggy region therein. The 3D endoscope apparatus further includes: a channel switch instruction portion that, when the image condition detection portion has detected a foggy region only in the video signal obtained from one of the first imaging system and the second imaging system, makes a switch to the other video signal; an image combining portion that, when the image condition detection portion has detected foggy regions in videos of both the first imaging system and the second imaging system, combines the first video signal and the second video signal to generate a composite image in which fogginess of the foggy regions has been reduced or eliminated; and a display portion that displays the 2D video signal and the 3D video signal.

A 3D endoscope apparatus according to one aspect of the disclosed technology includes: a video signal input portion to which a first video signal obtained by a first imaging system and a second video signal obtained by a second imaging system are inputted; and an image condition detection portion that analyzes a display area of a first image in the first video signal and/or a display area of a second image in the second video signal to detect a foggy region therein. The 3D endoscope apparatus further includes an image combining portion that, when the image condition detection portion has detected foggy regions in videos of both the first imaging system and the second imaging system, combines the first video signal and the second video signal to generate a composite image in which fogginess of the foggy regions has been reduced or eliminated. The 3D endoscope apparatus further includes a pseudo-3D conversion portion that simulatively converts, to a 3D video signal, a video signal without a foggy region obtained from one of the first imaging system and the second imaging system or the composite image generated by the image combining portion; and a display portion that displays the 3D video signal and a 2D video signal formed by one of the first video signal, the second video signal, and the composite image.

A 3D video processing apparatus according to one aspect of the disclosed technology includes: a video signal input portion to which a first video signal obtained by a first imaging system and a second video signal obtained by a second imaging system are inputted; and an image condition detection portion that analyzes a display area of a first image in the first video signal and/or a display area of a second image in the second video signal to detect a foggy region therein. The 3D video processing apparatus further includes: an image combining portion that, when the image condition detection portion has detected foggy regions in videos of both the first imaging system and the second imaging system, combines the first video signal and the second video signal to generate a composite image in which fogginess of the foggy regions has been reduced or eliminated; and an output portion that outputs a 2D video signal formed by one of the first video signal, the second video signal, and the composite image.

Hereinafter, embodiments of the disclosed technology will be described with reference to the accompanying drawings.

First Embodiment

FIG. 1 is a perspective view illustrating an example of the overall structure of an endoscope system including a 3D endoscope apparatus according to an embodiment of the disclosed technology. As illustrated in FIG. 1, an endoscope system 1 includes, as main components thereof, a 3D electronic endoscope (hereinafter referred to simply as an endoscope) 2 as an endoscopic scope, a lighting device 3, a processor 4 as a 3D video processing apparatus, and a monitor 5 as a display device.

The endoscope 2 includes a long, elongated insertion portion 9, an operating portion 10, and a universal cable 19 as an electric cable. The insertion portion 9 of the endoscope 2 includes a distal end portion 6, a bending portion 7, and a flexible tube portion 8 in this order from a distal end thereof.

A pair of objective lenses 23R and 23L are provided at two observation windows provided in the distal end portion 6. Solid-state imaging devices (not depicted), such as CCDs or complementary metal-oxide semiconductors (CMOSs), which are imaging devices having an optical-to-electrical conversion function, are disposed, as a first imaging system and a second imaging system, at image-forming positions of the objective lenses 23R and 23L. The pair of objective lenses 23R and 23L form right and left subject images of a subject in front, which have a parallax, on the solid-state imaging devices disposed at the respective image-forming positions.

A bending operation portion 14 for bending the bending portion 7 of the insertion portion 9 is rotatably arranged in the operating portion 10. In addition, the operating portion 10 is provided with switches and the like for various endoscope functions. As one of the switches and the like, a 2D/3D change switch 15 for switching the image to be displayed on the monitor 5 between a 2D endoscope image and a 3D endoscope image is provided in the operating portion 10. In the bending operation portion 14, a UD bending operation knob 12 for bending the bending portion 7 in an up-and-down direction, and an RL bending operation knob 13 for bending the bending portion 7 in a left-and-right direction are arranged in an overlapping manner.

In addition, a junction between the insertion portion 9 and the operating portion 10 has a graspable portion 11 that can be grasped by a user, and a treatment instrument channel insertion portion 18 arranged in a bending prevention portion provided between the graspable portion 11 and one end of the flexible tube portion 8 of the insertion portion 9. The treatment instrument channel insertion portion 18 is used as an opening portion of a treatment instrument channel arranged in the insertion portion 9 through which various types of treatment portions can be inserted.

The universal cable 19, which extends from the operating portion 10, has a scope connector 19a at a distal end thereof. The scope connector 19a is detachably connected to the lighting device 3. In addition, the scope connector 19a is provided with a coil-shaped coil cable 20, and a scope connector 20a as a connector detachably connected to the processor 4 is provided at a distal end of the coil cable 20. The endoscope 2 according to the present embodiment is configured to transfer an illuminating light from the lighting device 3 to the distal end portion 6 through the universal cable 19, the operating portion 10, and a light guide cable, which is lighting means arranged in the insertion portion 9.

The processor 4 as the 3D video processing apparatus is electrically connected to the monitor 5, which displays endoscope images. The processor 4 processes imaging signals obtained by optical-to-electrical conversion by imaging means, such as a CCD, installed in the endoscope 2, and outputs resulting image signals to the monitor 5.

Figure 2:
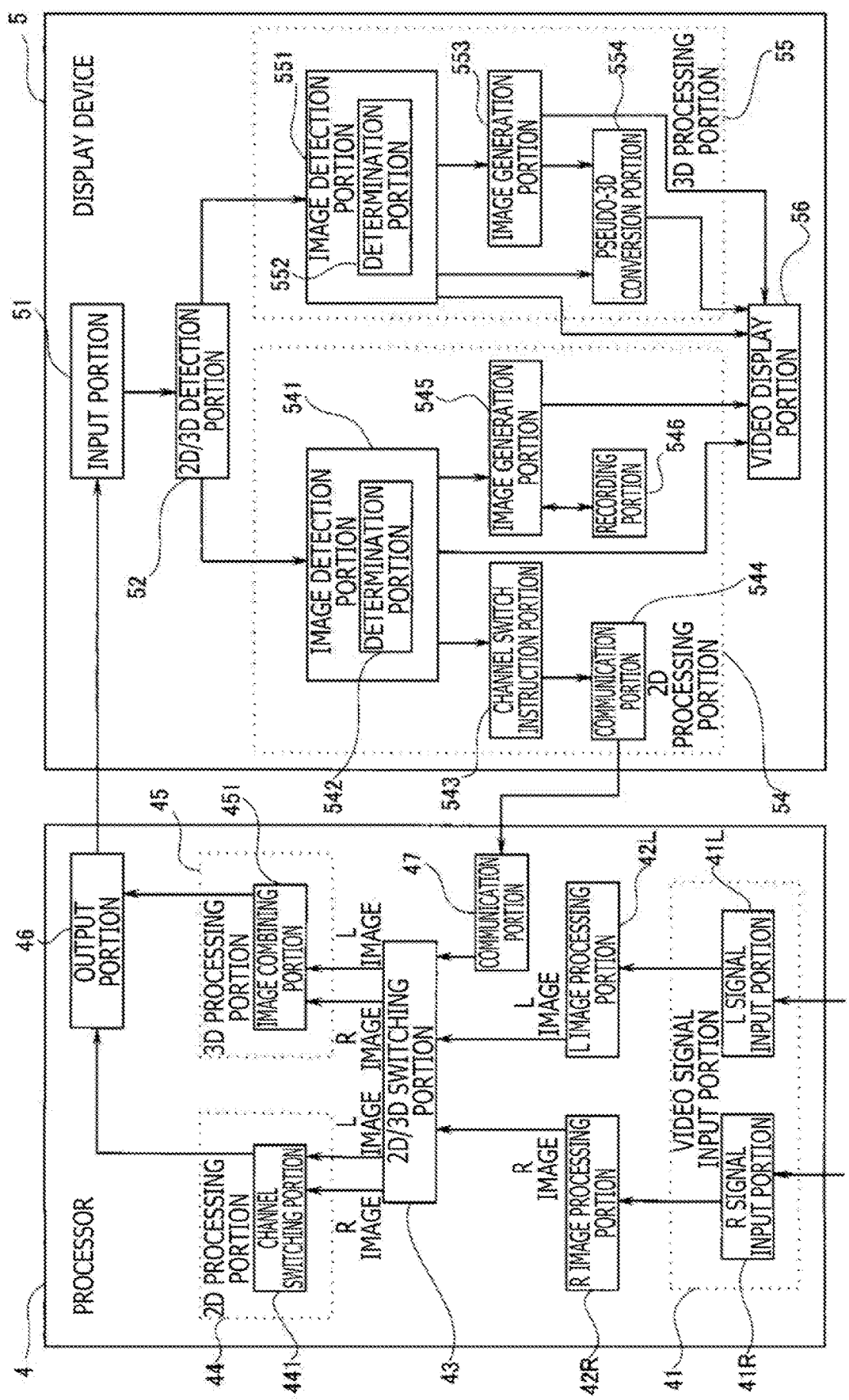
FIG. 2 is a block diagram for explaining example structures of a processor and a display device according to a first embodiment of the disclosed technology.

FIG. 2 is a block diagram for explaining example structures of the processor and the display device according to the first embodiment. The processor 4 includes a video signal input portion 41, an R image processing portion 42R, and an L image processing portion 42L. In addition, the processor 4 further includes a 2D/3D switching portion 43, a 2D processing portion 44, a 3D processing portion 45, an output portion 46, and a communication portion 47.

The video signal input portion 41 includes an R signal input portion 41R and an L signal input portion 41L. Images of a subject outputted from the endoscope 2 are inputted to the video signal input portion 41. Specifically, an image signal (hereinafter referred to as an R image signal) corresponding to a right eye is inputted to the R signal input portion 41R as a first video signal obtained by subjecting an image of the subject captured by the objective lens 23R to optical-to-electrical conversion in the solid-state imaging device. An image signal (hereinafter referred to as an L image signal) corresponding to a left eye is inputted to the L signal input portion 41L as a second video signal obtained by subjecting an image of the subject captured by the objective lens 23L to optical-to-electrical conversion in the solid-state imaging device.

The R image processing portion 42R performs various processes on the R image signal inputted from the R signal input portion 41R, and converts the R image signal to a signal that can be displayed on the monitor 5. The L image processing portion 42L performs various processes on the L image signal inputted from the L signal input portion 41L, and converts the L image signal to a signal that can be displayed on the monitor 5. Each of the R image processing portion 42R and the L image processing portion 42L includes, for example, a cadmium sulfide (CDS) circuit, a low-pass filter, a clamping circuit, an analog-digital (A/D) converter, a white balance correction circuit, a color adjustment circuit, a γ correction circuit, an edge enhancement circuit, and so on.

The 2D/3D switching portion 43 switches the output destination of the R image signal inputted from the R image processing portion 42R and the L image signal inputted from the L image processing portion 42L in accordance with an instruction inputted by an operator or the like using the 2D/3D change switch 15. Specifically, in the case where an instruction to display the 2D endoscope image on the monitor 5 is to be carried out, the 2D/3D switching portion 43 outputs the R image signal and the L image signal to the 2D processing portion 44. Meanwhile, in the case where an instruction to display the 3D endoscope image on the monitor 5 is to be carried out, the 2D/3D switching portion 43 outputs the R image signal and the L image signal to the 3D processing portion 45. In addition, the 2D/3D switching portion 43 inputs an instruction inputted from the monitor 5 via the communication portion 47 into the 2D processing portion 44.

When the L image signal and the R image signal have been inputted from the 2D/3D switching portion 43, the 2D processing portion 44 generates an image signal for a 2D endoscope image to be displayed on the monitor 5. The 2D processing portion 44 includes a channel switching portion 441. The channel switching portion 441 selects the R image signal or the L image signal inputted from the 2D/3D switching portion 43, and outputs the selected image signal to the output portion 46. Normally, the channel switching portion 441 selects and outputs the L image signal. If an instruction to switch the image signal is inputted from the 2D/3D switching portion 43, the channel switching portion 441 stops the output of the image signal currently being outputted, and outputs the other image signal. For example, if an instruction to switch the image signal is inputted while the L image signal is being outputted, the channel switching portion 441 stops the output of the L image signal, and outputs the R image signal.

When the L image signal and the R image signal have been inputted from the 2D/3D switching portion 43, the 3D processing portion 45 generates an image signal for a 3D endoscope image to be displayed on the monitor 5. The 3D processing portion 45 includes an image combining portion 451. The image combining portion 451 generates an image signal that complies with a 3D display system of the monitor 5 from the R image signal and the L image signal inputted thereto, and outputs the generated image signal to the output portion 46. For example, in the case where the monitor 5 is a 3D display that supports a polarized system, and dedicated polarized glasses are used to observe an image, it is necessary to transfer an image signal in a line-by-line format, or referred to also as an interlaced format. Accordingly, the image combining portion 451 extracts R image signals of even-numbered lines of each frame and L image signals of odd-numbered lines of each frame, and outputs the R image signals and the L image signals alternately. That is, an image signal of each frame is generated using L image signals as image signals of a first line, a third line, a fifth line, . . . , and a (2n−1)th line, and using R image signals as image signals of a second line, a fourth line, a sixth line, . . . , and a 2n-th line, and the generated image signal of each frame is outputted.

In the case where the 3D display system of the monitor 5 is another system, the image combining portion 451 generates and outputs an image signal that complies with that system. For example, in the case where the monitor 5 is a 3D display that supports a frame sequential system, and dedicated active shutter glasses are used to observe an image, it is necessary to transfer an image signal in a frame packing format. Accordingly, the image combining portion 451 outputs frames of L image signals and frames of R image signals alternately.

The output portion 46 outputs the image signals inputted from the 2D processing portion 44 or the 3D processing portion 45 to an input portion 51 of the monitor 5.

The communication portion 47 receives an instruction from the monitor 5, and outputs the received instruction to the 2D/3D switching portion 43.

The monitor 5 as a display device includes the input portion 51, a 2D/3D detection portion 52, a 2D processing portion 54, a 3D processing portion 55, and a video display portion 56. The input portion 51 receives the image signals outputted from the processor 4, and outputs the received image signals to the 2D/3D detection portion 52.

The 2D/3D detection portion 52 as a 2D/3D identification portion analyzes the inputted image signal, and identifies the inputted image signal as an image signal for a 2D endoscope image or an image signal for a 3D endoscope image. That is, in the case where the inputted image signal has been generated from only the L image signal or the R image signal, the 2D/3D detection portion 52 determines that the inputted image signal is an image signal for a 2D endoscope image. Meanwhile, in the case where the inputted image signal has been generated using both the L image signal and the R image signal, the 2D/3D detection portion 52 determines that the inputted image signal is an image signal for a 3D endoscope image.

In the case where the 2D/3D detection portion 52 has determined that the inputted image signal is an image signal for a 2D endoscope image, the 2D/3D detection portion 52 outputs the inputted image signal to the 2D processing portion 54. In the case where the 2D/3D detection portion 52 has determined that the inputted image signal is an image signal for a 3D endoscope image, the 2D/3D detection portion 52 outputs the inputted image signal to the 3D processing portion 55.

The 2D processing portion 54 detects whether or not a region (hereinafter referred to as a foggy region) corresponding to a fog or a stain on the lens is included in the inputted image signal for the 2D endoscope image, and when a foggy region has been detected, the 2D processing portion 54 corrects the foggy region to generate an image without a fog or a stain. The 2D processing portion 54 includes an image detection portion 541, a channel switch instruction portion 543, a communication portion 544, an image generation portion 545, and a recording portion 546.

Figure 3A:
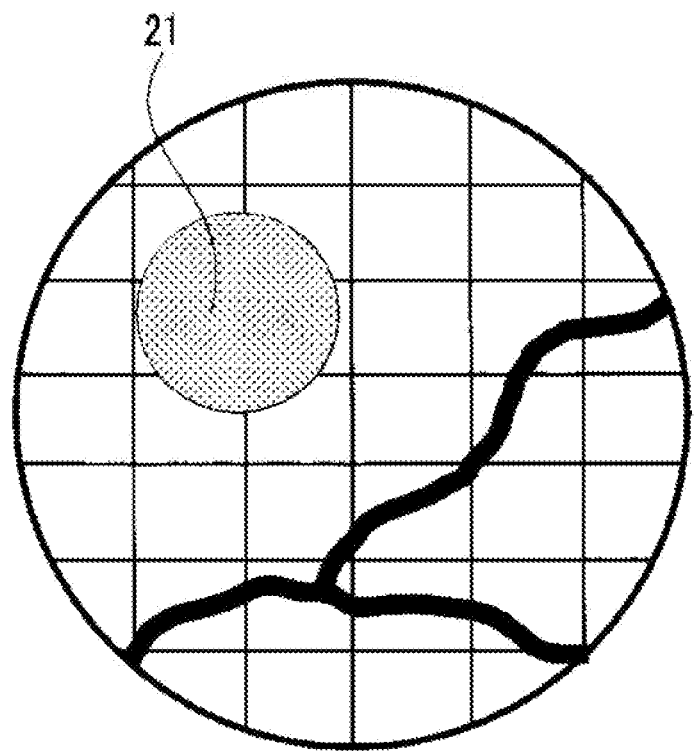
FIG. 3A is a diagram for explaining an example of an image including a fog.
Figure 3B:
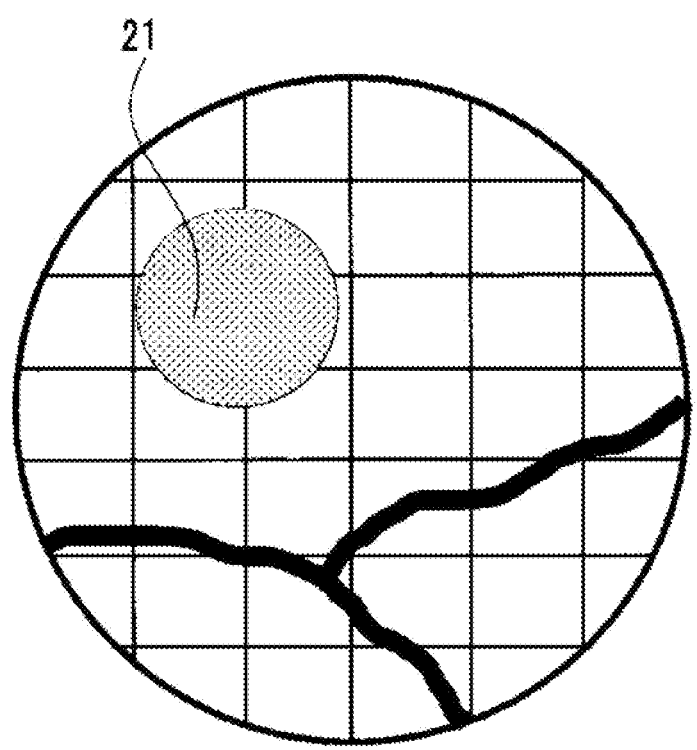
FIG. 3B is another diagram for explaining an example of an image including a fog.
Figure 4:
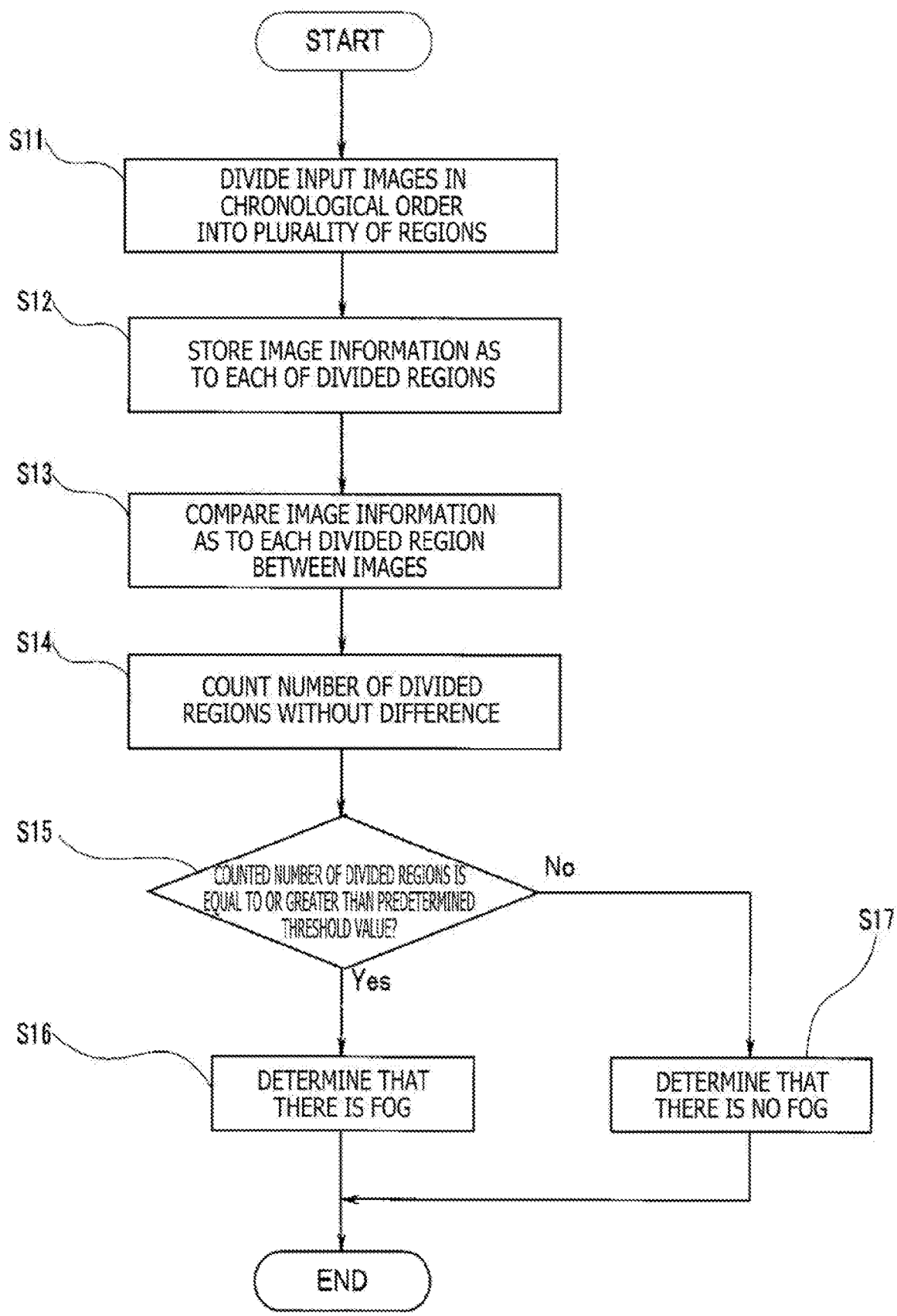
FIG. 4 is a flowchart for explaining an example procedure for detecting a fog in images.

The image detection portion 541 includes a determination portion 542 as an image condition detection portion. The determination portion 542 determines whether or not there is a foggy region in an endoscope image represented by the inputted image signal. FIGS. 3A, 3B, and 3C are diagrams for explaining examples of images including fogs. FIGS. 3A, 3B, and 3C are 2D endoscope images taken in this order at intervals of a predetermined time. That is, the endoscope image illustrated in FIG. 3A was taken first, and then, the endoscope image illustrated in FIG. 3B was taken the predetermined time (e.g., one second) later. The endoscope image illustrated in FIG. 3C was taken the predetermined time after the endoscope image illustrated in FIG. 3B was taken. The image signals inputted to the image detection portion 541 are recorded, as endoscope images, in the recording portion 546 at intervals of a predetermined time. FIG. 4 is a flowchart for explaining an example procedure for detecting a fog in images. The determination as to whether or not there is a foggy region in endoscope images will now be described hereinafter with reference to FIGS. 3A, 3B, 3C, and 4.

A plurality of endoscope images inputted in a chronological order, like the endoscope images illustrated in FIGS. 3A, 3B, and 3C, are first divided into a plurality of regions, and image information, or red-green-blue (RGB) pixel values, brightness information, hue information, etc., as to each of the divided regions is analyzed in S11. Next, the image information as to each divided region obtained as a result of the above analysis is stored in a memory (not depicted) in S12. In this memory, with respect to each divided region, pieces of image information of a predetermined number of frames, for example, are stored, and the pieces of image information are sequentially discarded after the elapse of a predetermined time.

When pieces of image information corresponding to a predetermined number of frames, or a predetermined time, have been stored in the memory, the determination portion 542 compares the pieces of image information between the frames, or between images, with respect to each divided region in S13. In this comparison, the RGB pixel values are normally used, but the hue information, which is not easily affected by an imaging position, imaging conditions, etc., may alternatively be used. As a result of the comparison, a divided region with respect to which the image information does not change for a duration corresponding to a predetermined number of frames, or the number of images corresponding to a predetermined time, i.e., differences in the image information between the frames or between the images are substantially zero, is detected as a fog-including region, and the number of fog-including regions detected is counted in S14. For example, in the case where a shaded portion 21 in an upper part of the image in each of FIGS. 3A, 3B, and 3C includes a fog, six divided regions that include a part of the shaded portion 21 are counted as fog-including regions.

If the number of fog-including regions counted in S14 is equal to or greater than a predetermined threshold value set in advance, Yes in S15, it is determined that there is a foggy region in the endoscope images in S16. Meanwhile, if the number of fog-including regions counted in S14 is smaller than the predetermined threshold value set in advance, No in S15, it is determined that there is no foggy region in the endoscope images in S17. Note that the threshold value used in the determination is set appropriately in accordance with the size and number of divided regions. If the threshold value is set to be three in the case of FIGS. 3A, 3B, and 3C, for example, it is determined that there is a foggy region because the number of fog-including regions is six.

In the case where the determination portion 542 has determined that there is no foggy region, the image detection portion 541 outputs the image signals currently inputted to the video display portion 56. Meanwhile, in the case where the determination portion 542 has determined that there is a foggy region, the image detection portion 541 stores the image signals currently inputted in the recording portion 546.

In the case where it has been determined in the image detection portion 541 that there is a foggy region in the input images, the channel switch instruction portion 543 generates an instruction signal representing an instruction to output image signals of a channel different from that of the image signals currently being inputted, and outputs the generated instruction signal to the communication portion 544. For example, in the case where the L image signals are being inputted from the processor 4 to the monitor 5, and it has been determined that there is a foggy region in the endoscope images represented by the L image signals, the channel switch instruction portion 543 generates an instruction signal representing an instruction to stop the output of the L image signals and instead output the R image signals, and outputs the generated instruction signal to the communication portion 544. Once the instruction signal is inputted from the channel switch instruction portion 543 to the communication portion 544, the communication portion 544 outputs this instruction signal to the communication portion 47 of the processor 4.

Figure 5:
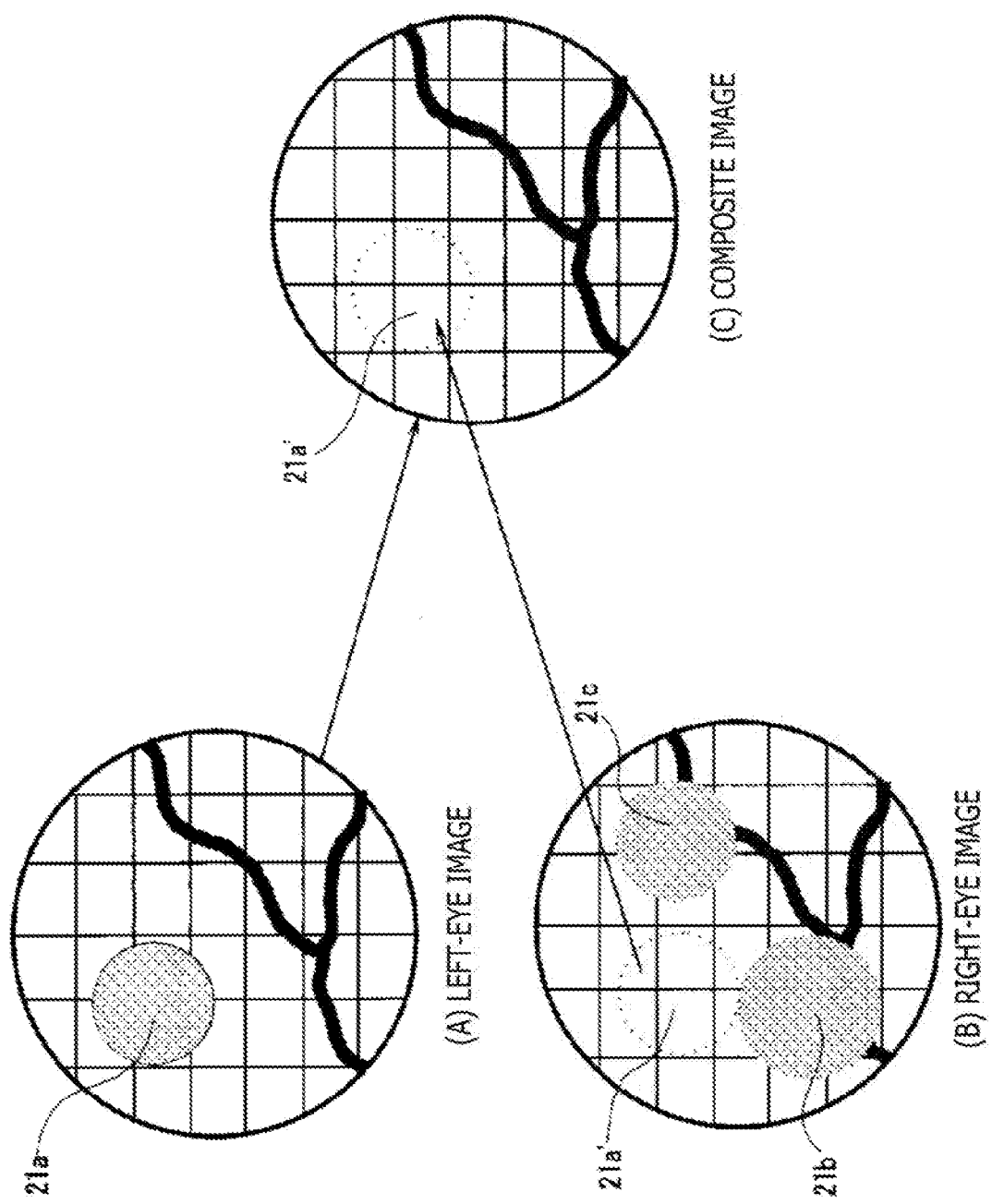
FIG. 5 is a diagram for explaining an example image which is generated from right-eye and left-eye images including a fog and from which the fog has been eliminated.

The image generation portion 545 as an image combining portion uses the image signals currently inputted and the images stored in the recording portion 546 to generate images in which the foggy region has been corrected. FIG. 5 is a diagram for explaining an example image which is generated from right-eye and left-eye images including a fog and from which the fog has been eliminated. Here, (A) of FIG. 5 illustrates a left-eye endoscope image represented by an L image signal, (B) of FIG. 5 illustrates a right-eye endoscope image represented by an R image signal, and (C) of FIG. 5 illustrates a composite image which has been generated using the images illustrated in (A) and (B) of FIG. 5 and in which the foggy region has been corrected.

In the case where the left-eye endoscope image represented by the L image signal includes a foggy region 21a as illustrated in (A) of FIG. 5, the R image signal is acquired in place of the L image signal with an instruction issued to the processor 4. In the case where the right-eye endoscope image ((B) of FIG. 5) represented by the acquired R image signal includes foggy regions 21b and 21c, the image generation portion 545 compares the left-eye endoscope image ((A) of FIG. 5) stored in the recording portion 546 with the right-eye endoscope image ((B) of FIG. 5) currently acquired, and selects the image with a smaller number of foggy regions as a base image. In the case of the example illustrated in FIG. 5, the left-eye endoscope image ((A) of FIG. 5) has one foggy region, and the right-eye endoscope image ((B) of FIG. 5) has two foggy regions, and therefore, the left-eye endoscope image illustrated in (A) of FIG. 5 is selected as the base image.

The image generation portion 545 extracts a region corresponding to the foggy region in the base image from the other endoscope image. In the case of the example illustrated in FIG. 5, a region 21a' corresponding to the foggy region 21a in (A) of FIG. 5 is extracted from the right-eye endoscope image ((B) of FIG. 5), which corresponds to the other endoscope image. In the case where the extracted region is not a foggy region, the foggy region in the base image is corrected with an image of the extracted region 21a' to generate the composite image, or an image without a foggy region. Meanwhile, in the case where the extracted region is also a foggy region, an error message (for example, a message that suggests that the lenses are to be cleaned) is generated because it is not possible to correct the foggy region in the base image. The image generation portion 545 outputs the generated composite image or the generated error message to the video display portion 56.

The 3D processing portion 55 detects whether or not a foggy region is included in the inputted image signal for the 3D endoscope image, and when a foggy region has been detected, the 3D processing portion 55 corrects the foggy region to generate an image without a fog or a stain. The 3D processing portion 55 includes an image detection portion 551, an image generation portion 553, and a pseudo-3D conversion portion 554.

The image detection portion 551 separates the inputted image signal into the L image signal and the R image signal. The image detection portion 551 includes a determination portion 552. The determination portion 552 determines whether or not there is a foggy region in each of the endoscope images, or the left-eye endoscope image and the right-eye endoscope image, generated using the L image signal and the R image signal. A method employed by the determination portion 552 to determine whether or not there is a foggy region is similar to the method employed by the determination portion 542 to determine whether or not there is a foggy region.

In the case where it has been determined in the determination portion 552 that neither the left-eye endoscope image nor the right-eye endoscope image includes a foggy region, the image detection portion 551 outputs the inputted image signal as it is, or the image signal before being separated into the L image signal and the R image signal, to the video display portion 56.

Meanwhile, in the case where it has been determined in the determination portion 552 that only one of the left-eye endoscope image and the right-eye endoscope image includes a foggy region, the image detection portion 551 outputs, to the pseudo-3D conversion portion 554, the image signal for the image that has been determined to include no foggy region. For example, in the case where it has been determined that the left-eye endoscope image includes no foggy region and the right-eye endoscope image includes a foggy region, the L image signal for the left-eye endoscope image is outputted to the pseudo-3D conversion portion 554.

Further, in the case where it has been determined in the determination portion 552 that both the left-eye endoscope image and the right-eye endoscope image include foggy regions, the image detection portion 551 outputs the L image signal and the R image signal to the image generation portion 553.

The image generation portion 553 generates an image in which the foggy region has been corrected using the L image signal and the R image signal. Specifically, the image generation portion 553 generates a composite image in which the foggy region has been corrected by a procedure similar to the procedure by which the corrected image is generated by the image generation portion 545, which has been described hereinbefore with reference to FIG. 5. Here, in the case where the left-eye endoscope image is used as a base image, the composite image generated by the image generation portion 553 is a left-eye endoscope image. Meanwhile, in the case where the right-eye endoscope image is used as a base image, the composite image generated by the image generation portion 553 is a right-eye endoscope image. In the case where a foggy region in the base image cannot be corrected, an error message (e.g., a message that suggests that the lenses are to be cleaned) is generated.

In the case where the image generation portion 553 has generated the composite image, the image generation portion 553 outputs an image signal of this composite image to the pseudo-3D conversion portion 554. In the case where a left-eye endoscope image has been generated as the composite image, the image signal of the composite image is outputted as an L image signal. In the case where a right-eye endoscope image has been generated as the composite image, an image signal of the composite image is outputted as an R image signal. In the case where the error message has been generated, the image generation portion 553 outputs this message to the video display portion 56.

The pseudo-3D conversion portion 554 simulatively generates another image signal from the inputted image signal. That is, in the case where the L image signal has been inputted to the pseudo-3D conversion portion 554, the pseudo-3D conversion portion 554 generates an R image signal using the L image signal. In the case where the R image signal has been inputted to the pseudo-3D conversion portion 554, the pseudo-3D conversion portion 554 generates an L image signal using the R image signal. A well-known method commonly used to generate a pseudo-3D image signal from a 2D image signal can be adopted here. For example, in the case where an R image signal is generated from an L image signal, the pixel position of each of pixels of a left-eye endoscope image generated from the L image signal is shifted horizontally to the right by a distance corresponding to a parallax. In the case where the parallax between the left-eye endoscope image and the right-eye endoscope image corresponds to 10 pixels, for example, the pixels in an nth column of the left-eye endoscope image are shifted to an (n+10)th column in the same rows. Note that, in addition to shifting the positions of the pixels of the whole image horizontally by the distance corresponding to the parallax, the image may be corrected so as to emphasize the depth of a local pixel area, such as of a fold of a wall, a blood vessel, a tumor, etc., in the image, to simulatively generate an image signal. This will result in an image signal of a pseudo-3D endoscope image with an enhanced three-dimensional effect.

The R image signal is simulatively generated using the L image signal without a foggy region, or the L image signal is simulatively generated using the R image signal without a foggy region, as described hereinbefore, so that the L image signal and the R image signal necessary to produce a 3D endoscope image without a foggy region are obtained. Then, an image signal that complies with the 3D display system of the monitor 5 is generated from the inputted image signal and the image signal generated simulatively in a manner similar to that employed by the image combining portion 451, and is outputted to the video display portion 56.

The video display portion 56 as a display portion causes the inputted image signal to be displayed as an image on a screen.

Figure 6:
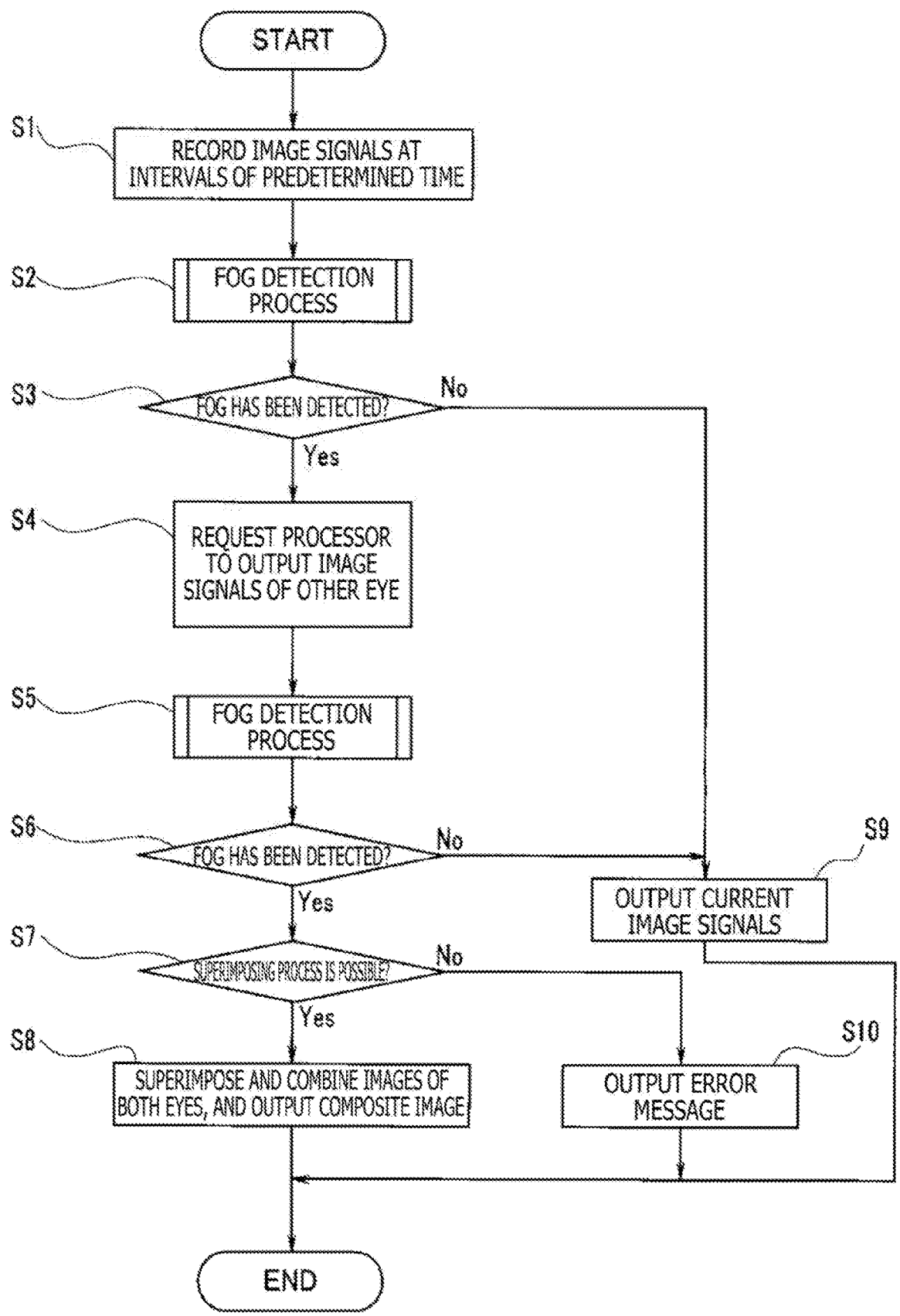
FIG. 6 is a flowchart for explaining an example procedure by which a 2D image is generated according to the first embodiment.

Next, a procedure by which a 2D/3D endoscope image is generated in the monitor 5 of the 3D endoscope apparatus according to the present embodiment will now be described hereinafter. FIG. 6 is a flowchart for explaining an example procedure by which a 2D image is generated according to the first embodiment. First, a procedure by which the 2D endoscope image is generated is described with reference to FIG. 6. First, the image detection portion 541 records the image signals (e.g., the L image signals) inputted from the processor 4 at intervals of a predetermined time set in advance in S1.

Next, the image detection portion 541 detects whether there is a foggy region in the images recorded in S2. A fog detection process in S2 is performed by performing the series of steps S11 to S17 illustrated in FIG. 4.

If no foggy region is detected in the images in S2, No in S3, the image signals currently being inputted are outputted to the video display portion 56 in S9, and the process is ended. Meanwhile, if a foggy region is detected in the images in S2, Yes in S3, the output of the image signals currently being inputted is stopped, and an instruction to output the image signals of the other eye is issued to the processor 4 in S4. For example, in the case where the L image signals are being inputted, and a foggy region has been detected in the images thereof, the channel switch instruction portion 543 issues an instruction to output the R image signals in place of the L image signals to the processor 4 via the communication portion 544.

When the image signals of the other eye (e.g., the R image signals) have been inputted from the processor 4, the image detection portion 541 detects whether there is a foggy region in the image signals in S5. A fog detection process in S5 is similar to the fog detection process in S2. If no foggy region is detected in the images in S5, No in S6, the image signals currently being inputted are outputted to the video display portion 56 in S9, and the process is ended. Meanwhile, if a foggy region is detected in the images in S5, Yes in S6, the image generation portion 545 determines whether or not a composite image in which the foggy region has been corrected can be generated by superimposing the image signal currently being inputted and an image signal of the other eye stored in the recording portion 546 in S7.

If it is determined that the composite image can be generated by superimposing the image signals of both eyes, Yes in S7, the image generation portion 545, using the L image signal and the R image signal, corrects the foggy region on the base image by superimposing the other image thereon, thus generating a composite image without a foggy region, and outputs the composite image to the video display portion 56 in S8, so that the series of processes is ended. Meanwhile, if it is determined that it is not possible to generate the composite image, No in S7, the image generation portion 545 outputs an error message that suggests that the lenses are to be cleaned to the video display portion 56 in S10, and the process is ended.

Figure 7:
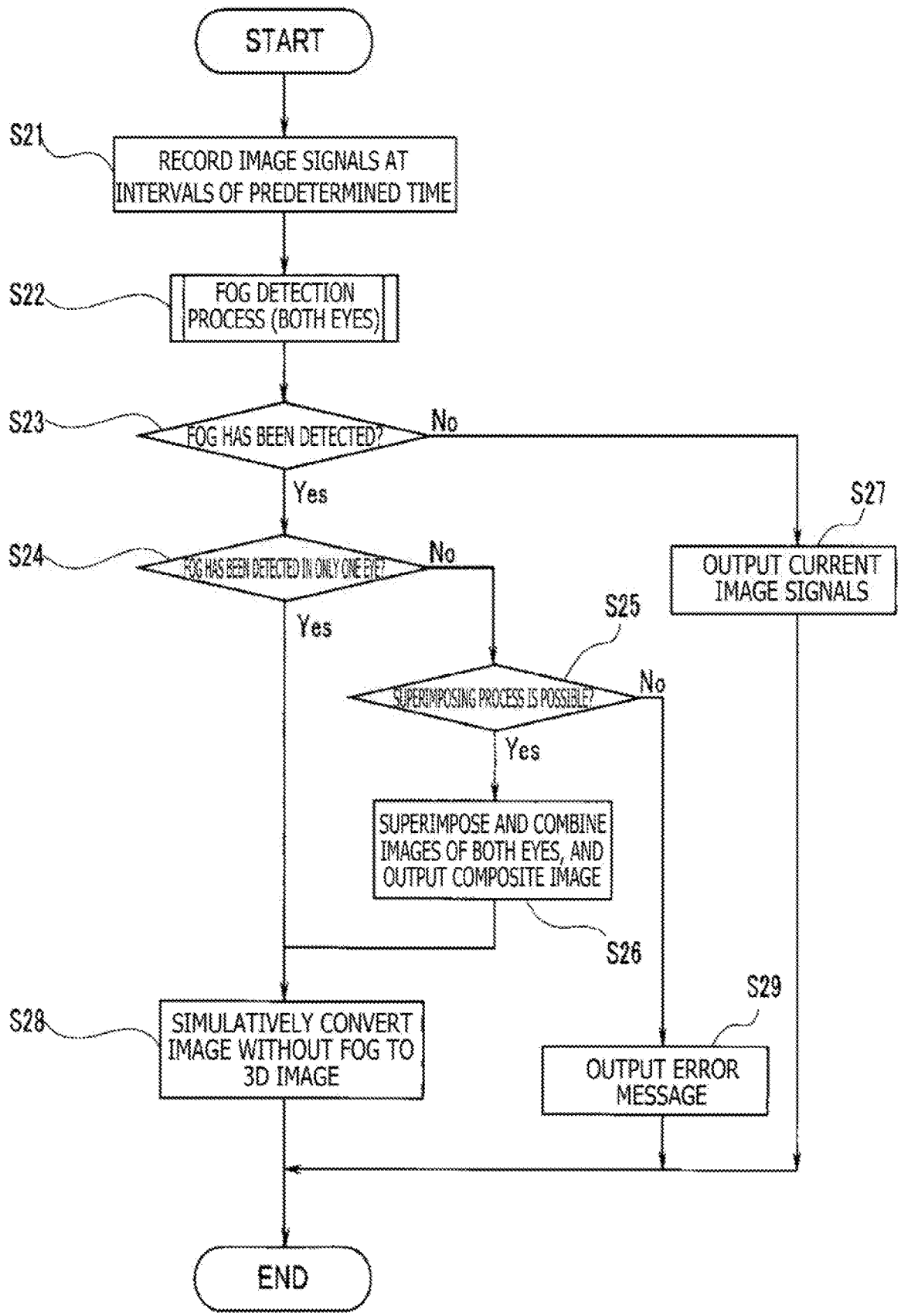
FIG. 7 is a flowchart for explaining an example procedure by which a 3D image is generated.

FIG. 7 is a flowchart for explaining an example procedure by which a 3D image is generated. Next, a procedure by which the 3D endoscope image is generated is described with reference to FIG. 7. First, the image detection portion 551 records the image signals inputted from the processor 4 at intervals of a predetermined time set in advance in S21.

Next, the image detection portion 551 separates the recorded image signals into the L image signals and the R image signals, and detects whether there is a foggy region in the images of both eyes in S22. A fog detection process in S22 is performed by performing the series of steps S11 to S17 illustrated in FIG. 4.

If no foggy region is detected in the images of either eye in S22, No in S23, the image signals currently being inputted are outputted to the video display portion 56 in S27, and the process is ended. Meanwhile, if a foggy region is detected in the images in S22, Yes in S23, it is determined whether a foggy region has been detected in only the images of the image signals of one of the eyes or in the images of the image signals of both eyes in S24.

In the case where a foggy region has been detected in only the image signals of one of the eyes, Yes in S24, the image detection portion 551 outputs the image signal without a foggy region to the pseudo-3D conversion portion 554. The pseudo-3D conversion portion 554 simulatively generates an image signal of the other eye from the inputted image signal. Then, an image signal that complies with the 3D display system of the monitor 5 is generated from the inputted image signal and the image signal generated simulatively, and is outputted to the video display portion 56 in S28.

Meanwhile, in the case where foggy regions have been detected in the image signals of both eyes, No in S24, the image detection portion 551 outputs the image signals of both eyes to the image generation portion 553. The image generation portion 553 determines whether or not a composite image in which the foggy region has been corrected can be generated by superimposing the image signals of both eyes in S25.

If it is determined that the composite image can be generated by superimposing the image signals of both eyes, Yes in S25, the image generation portion 553, using the image signals of both eyes, corrects the foggy region on the base image by superimposing the other image thereon, thus generating a composite image without a foggy region, and outputs the composite image to the pseudo-3D conversion portion 554 in S26.

An image signal of the composite image outputted at this time is outputted as an image signal of the base image. For example, in the case where the left-eye endoscope image has been selected as the base image, the composite image is outputted as an L image signal. From the image signal inputted to the pseudo-3D conversion portion 554, an image signal of the other eye is simulatively generated. Then, an image signal that complies with the 3D display system of the monitor 5 is generated from the inputted image signal and the image signal generated simulatively, and is outputted to the video display portion 56 in S28.

Meanwhile, if it is determined that it is not possible to generate the composite image, No in S25, the image generation portion 553 outputs an error message that suggests that the lenses are to be cleaned to the video display portion 56 in S29, and the process is ended.

As described hereinbefore, the 3D endoscope apparatus according to the present embodiment is provided with the determination portions 542 and 552, each of which detects whether or not there is a foggy region from the inputted image signals. If, while a 2D endoscope image is displayed, the determination portion 542 detects a foggy region in the image being displayed, a 2D endoscope image is generated using an image signal of the other eye. In addition, in the case where there are fogs on both the lenses, the image generation portion 545 generates one 2D endoscope image by combining fog-free regions of the left-eye endoscope image and the right-eye endoscope image. Therefore, even in the case where there is a fog on either objective lens or a stain has been attached to either objective lens, a clear endoscope image can be outputted without the need to interrupt a manipulation.

Meanwhile, if, while a 3D endoscope image is displayed, the determination portion 552 detects a foggy region in the image being displayed, the pseudo-3D conversion portion 554 generates an image signal for the lens on which there is a fog by converting the image signal for the other lens on which there is no fog. Then, a 3D endoscope image is generated using the generated image signal and the image signal for the other lens.

In addition, in the case where there are fogs on both the lens, the image generation portion 553 generates an image signal for the lens having a smaller number of foggy regions by combining fog-free regions of the left-eye endoscope image and the right-eye endoscope image. Then, an image signal for the other lens is generated in the pseudo-3D conversion portion 554 by using the image signal generated by the image generation portion 553. A 3D endoscope image is generated using the image signal generated by the image generation portion 553 and the image signal generated by the pseudo-3D conversion portion 554. Therefore, even in the case where there are fogs on the objective lenses or stains have been attached to the objective lenses, a clear endoscope image can be outputted without the need to interrupt a manipulation.

In each of the image generation portions 545 and 553, the foggy region in the endoscope image taken with the lens having a smaller number of foggy regions is corrected using the endoscope image taken with the other lens, and this may result in a reduction in image quality of the endoscope image generated. It is therefore desirable that the 3D endoscope apparatus according to an embodiment of the disclosed technology is used not for a close examination, but in a situation that does not require a very high level of fineness, such as in a scene of broadly viewing an operative field, a scene of screening, or the like.

Second Embodiment

In the 3D endoscope apparatus according to the first embodiment described hereinbefore, an instruction to display the 2D endoscope image or the 3D endoscope image on the monitor 5 is inputted to the processor 4 by an operator or the like using the 2D/3D change switch 15, and in accordance with this instruction, the processor 4 generates a 2D image signal or a 3D image signal, and outputs the 2D image signal or the 3D image signal to the monitor 5. A second embodiment of the disclosed technology is different from the first embodiment in that 3D image signals are always outputted from a processor 4' to a monitor 5', and that the instruction to display the 2D endoscope image or the 3D endoscope image on the monitor 5' is inputted to the monitor 5', and an image is generated in the monitor 5' in accordance with the instruction.

Figure 8:
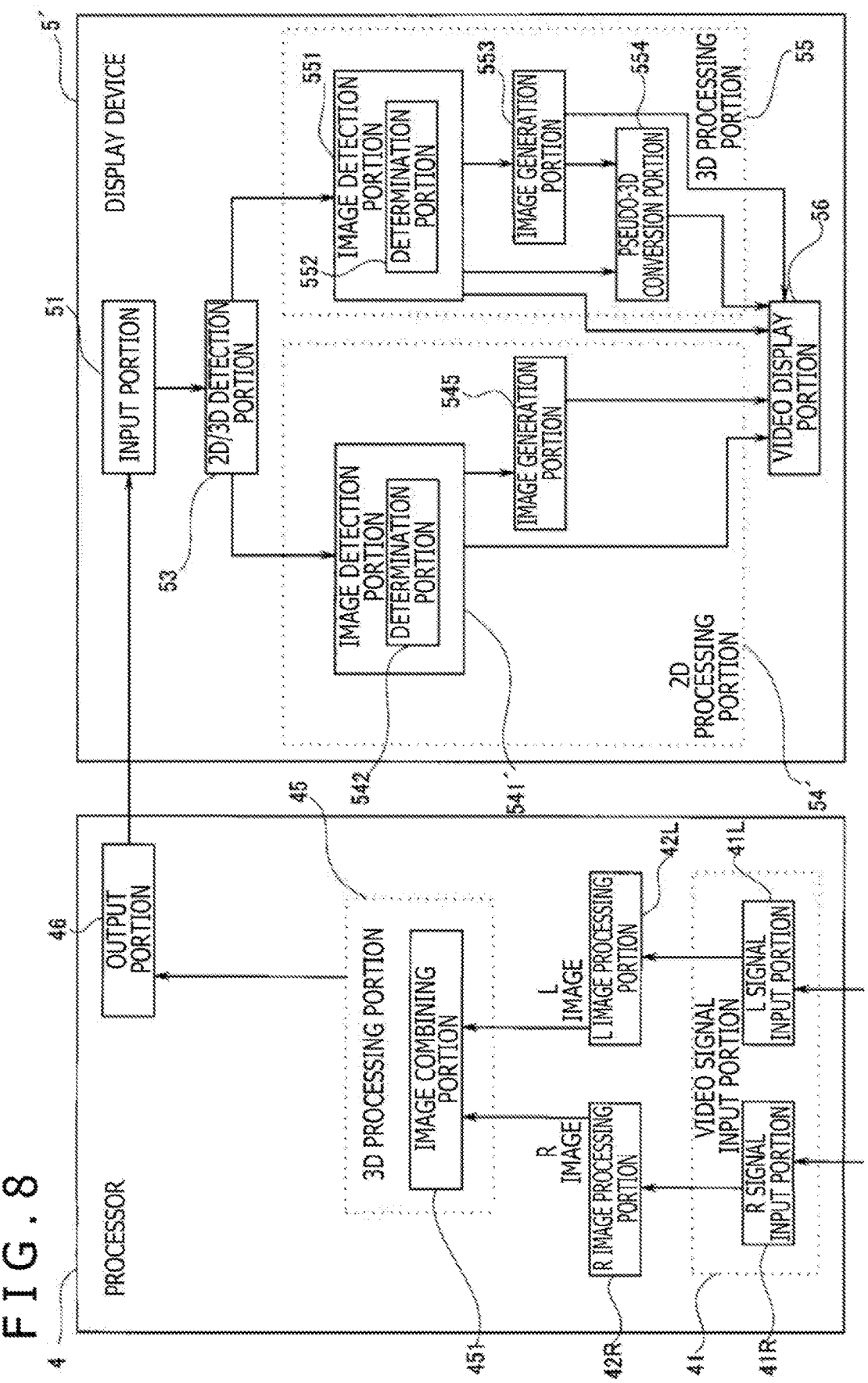
FIG. 8 is a block diagram for explaining example structures of a processor and a display device according to a second embodiment of the disclosed technology.

FIG. 8 is a block diagram for explaining example structures of the processor and the display device according to the second embodiment. A 3D endoscope apparatus according to the present embodiment is similar to the 3D endoscope apparatus according to the first embodiment, which has been described hereinbefore with reference to FIG. 2, except in that the processor 4' does not include any of the 2D/3D switching portion 43, the 2D processing portion 44, and the communication portion 47, that a 2D processing portion 54' of the monitor 5' does not include either of the channel switch instruction portion 543 and the communication portion 544, and that a 2D/3D switching portion 53 is provided in place of the 2D/3D detection portion 52. The same parts are designated by the same numeral references, and redundant description will be omitted.

The processor 4' performs various types of image processing on an L image signal and an R image signal inputted from the endoscope 2, and thereafter generates an image signal (e.g., an interlaced image signal) for a 3D endoscope image in a 3D processing portion 45. The image signal for the 3D endoscope image is inputted to an input portion 51 of the monitor 5' via an output portion 46.

The 2D/3D switching portion 53 of the monitor 5' switches the output destination of the image signal for the 3D endoscope image inputted to the input portion 51 in accordance with an instruction inputted by an operator or the like using the 2D/3D change switch 15. That is, in the case where an instruction to display a 2D endoscope image is to be carried out, the 2D/3D switching portion 53 outputs the image signal for the 3D endoscope image to the 2D processing portion 54'. Meanwhile, in the case where an instruction to display a 3D endoscope image is to be carried out, the 2D/3D switching portion 53 outputs the image signal for the 3D endoscope image to a 3D processing portion 55.

The 2D processing portion 54' separates an L image signal and an R image signal from the inputted image signal for the 3D endoscope image. The 2D processing portion 54' detects whether or not a region (hereinafter referred to as a foggy region) corresponding to a fog or a stain on the lens is included in each of the image signals, and when a foggy region has been detected, the 2D processing portion 54' corrects the foggy region to generate an image without a fog or a stain. The 2D processing portion 54' includes an image detection portion 541' and an image generation portion 545.

The image detection portion 541' determines whether or not there is a foggy region in one of the image signals which has been specified in advance (the L image signal has normally been specified because the left-eye endoscope image is normally displayed as the 2D endoscope image). In the case where a determination portion 542 has determined that there is no foggy region therein, this image signal (e.g., the L image signal) is outputted to a video display portion 56. Meanwhile, in the case where the determination portion 542 has determined that there is a foggy region therein, it is determined whether or not there is a foggy region in the other image signal (in the example described hereinbefore, the R image signal). In the case where the determination portion 542 has determined that there is no foggy region therein, this image signal (e.g., the R image signal) is outputted to the video display portion 56.

Meanwhile, in the case where it has been determined that there is a foggy region in the other image signal as well, the image detection portion 541' outputs the image signals of both eyes to the image generation portion 545. The image generation portion 545 generates an image in which the foggy region has been corrected using the L image signal and the R image signal inputted thereto. The image generation portion 545 outputs the generated composite image or an error message to the video display portion 56.

The structure and functions of the 3D processing portion 55 are similar to those of the 3D processing portion 55 according to the first embodiment, which has been described hereinbefore with reference to FIG. 2.

Figure 9:
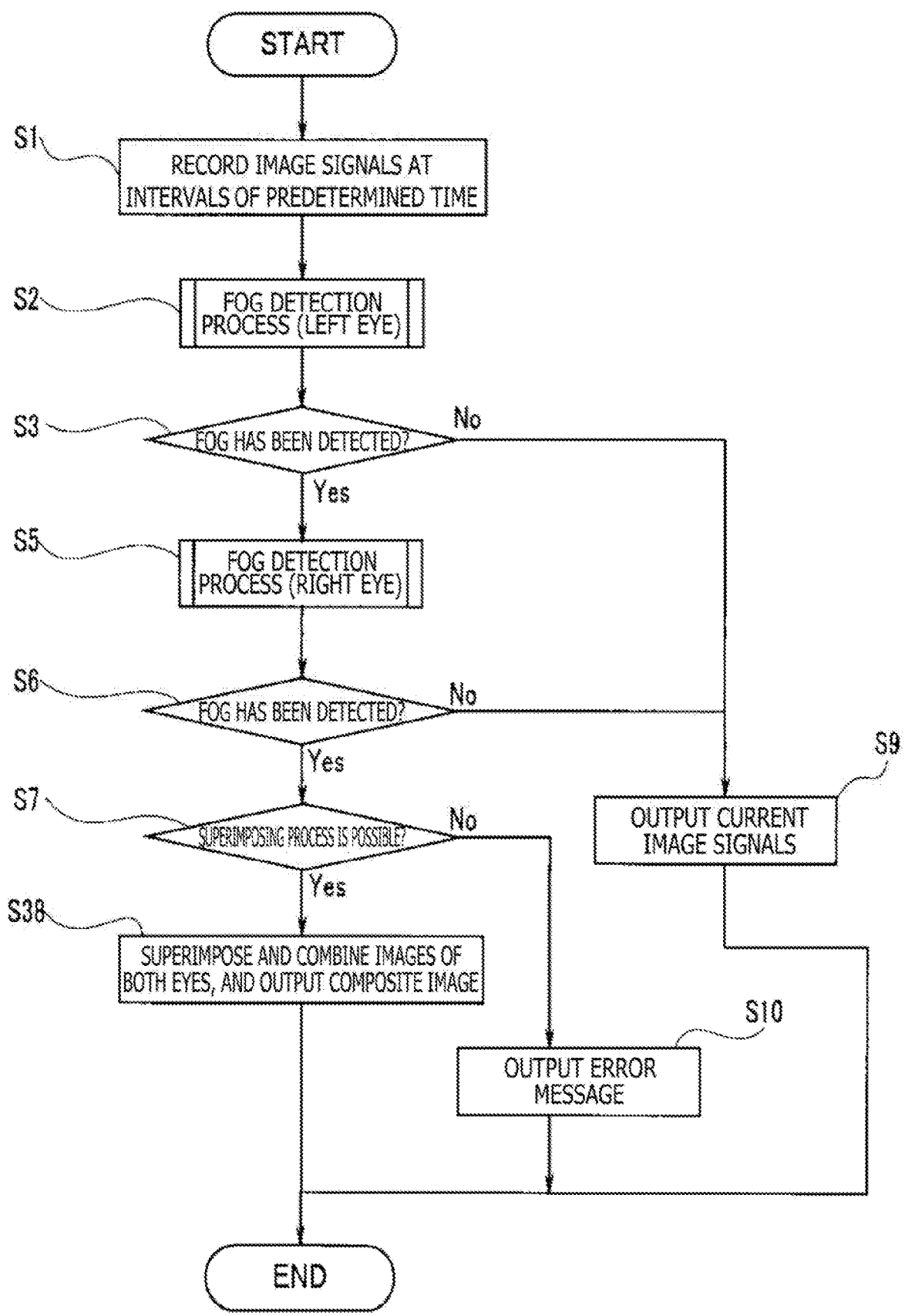
FIG. 9 is a flowchart for explaining an example procedure by which a 2D image is generated according to the second embodiment.

Next, a procedure by which the 2D endoscope image is generated in the monitor 5' of the 3D endoscope apparatus according to the present embodiment will now be described hereinafter. A procedure by which the 3D endoscope image is generated is similar to the procedure described hereinbefore with reference to the flowchart of FIG. 7. FIG. 9 is a flowchart for explaining an example procedure by which a 2D image is generated according to the second embodiment. First, the image detection portion 541' separates each of the 3D image signals inputted from the processor 4' into an L image signal and an R image signal, and records the L and R image signals at intervals of a predetermined time set in advance in S1.

Next, the image detection portion 541' detects whether there is a foggy region in the image signals (e.g., the L image signals) of one of the eyes which has been specified in advance in S2. If no foggy region is detected in the images in S2, No in S3, the image signals currently being inputted are outputted to the video display portion 56 in S9, and the process is ended. Meanwhile, if a foggy region is detected in the images in S2, Yes in S3, it is detected whether there is a foggy region in the image signals (e.g., the R image signals) of the other eye in S5. A fog detection process in S5 is similar to the fog detection process in S2. If no foggy region is detected in the images in S5, No in S6, the image signals currently being inputted are outputted to the video display portion 56 in S9, and the process is ended. Meanwhile, if a foggy region is detected in the images in S5, Yes in S6, the image generation portion 545 determines whether or not a composite image in which the foggy region has been corrected can be generated by superimposing the image signal currently being inputted and an image signal of the other eye stored in a recording portion 546 in S7.

If it is determined that the composite image can be generated by superimposing the image signals of both eyes, Yes in S7, the image generation portion 545, using the L image signal and the R image signal separated from the inputted 3D image signal, corrects the foggy region on the base image by superimposing a corresponding region of the other image thereon. The image generation portion 545 thus generates a composite image without a foggy region, and outputs the composite image to the video display portion 56 in S38, so that the series of processes is ended. Meanwhile, if it is determined that it is not possible to generate the composite image, No in S7, the image generation portion 545 outputs an error message that suggests that the lenses are to be cleaned to the video display portion 56 in S10, and the process is ended.

As described hereinbefore, according to the present embodiment, even in the case where there is a fog on the objective lens or a stain has been attached to the objective lens, the 2D processing portion 54' and the 3D processing portion 55 are configured to selectively output the endoscope image of one of the eyes without a fog, generate a composite image without a fog by combining fog-free regions of the left-eye endoscope image and the right-eye endoscope image, or generate a pseudo-3D image using the composite image or the endoscope image of one of the eyes without a fog. Thus, a clear endoscope image can be outputted without the need to interrupt a manipulation.

In addition, according to the present embodiment, the image signals for the 3D endoscope images, that is, both the L image signals and the R image signals, are always inputted from the processor 4' to the monitor 5'. Therefore, even if a foggy region is detected in the image signals of one of the eyes when image signals without a fog are generated in the 2D processing portion 54', it is not necessary to request the processor 4' to send the image signals of the other eye. This leads to a reduction in communication between the processor 4' and the monitor 5', a simplified procedure for processing, and a reduction in processing time. In addition, reductions in both the number of components of the processor 4' and the number of components of the monitor 5' can be achieved, resulting in a reduced size of the 3D endoscope apparatus.

Third Embodiment

In the 3D endoscope apparatus according to the second embodiment described hereinbefore, the image signals without a fog are generated in the 2D processing portion 54' and the 3D processing portion 55 of the monitor 5' using the image signals inputted from the processor 4'. A third embodiment of the disclosed technology is different from the second embodiment in that image signals without a fog are generated in a 2D processing portion 44' and a 3D processing portion 45' of a processor 4".

FIG. 10 is a block diagram for explaining an example structure of the processor according to the third embodiment. The processor 4" according to the present embodiment, which is a 3D video processing apparatus, is similar to the processor 4' according to the second embodiment, which has been described hereinbefore with reference to FIG. 8, except in that a 2D/3D switching portion 43 is provided, that the structure of the 2D processing portion 44' is identical to that of the 2D processing portion 54' of the monitor 5' illustrated in FIG. 8, and that the structure of the 3D processing portion 45' is identical to that of the 3D processing portion 55 of the monitor 5' illustrated in FIG. 8. The same parts are designated by the same numeral references, and redundant description will be omitted.

In the case where an instruction to display a 2D endoscope image on a monitor 5" has been issued with the 2D/3D change switch 15, an R image signal and an L image signal outputted from the endoscope 2 and subjected to various types of image processing are inputted from the 2D/3D switching portion 43 to the 2D processing portion 44'.

The 2D processing portion 44' detects whether or not a region (hereinafter referred to as a foggy region) corresponding to a fog or a stain on the lens is included in each of the L image signal and the R image signal inputted thereto, and when a foggy region has been detected, the 2D processing portion 44' corrects the foggy region to generate an image without a fog or a stain. The 2D processing portion 44' includes an image detection portion 541' and an image generation portion 545.

The image detection portion 541' determines whether or not there is a foggy region in one of the image signals which has been specified in advance (the L image signal has normally been specified because the left-eye endoscope image is normally displayed as the 2D endoscope image). In the case where a determination portion 542 has determined that there is no foggy region therein, this image signal (e.g., the L image signal) is outputted to an output portion 46. Meanwhile, in the case where the determination portion 542 has determined that there is a foggy region therein, it is determined whether or not there is a foggy region in the other image signal (in the example described hereinbefore, the R image signal). In the case where the determination portion 542 has determined that there is no foggy region therein, this image signal (e.g., the R image signal) is outputted to the output portion 46.

Meanwhile, in the case where it has been determined that there is a foggy region in the other image signal as well, the image detection portion 541' outputs the image signals of both eyes to the image generation portion 545. The image generation portion 545 generates an image in which the foggy region has been corrected using the L image signal and the R image signal inputted thereto. The image generation portion 545 outputs the generated composite image or an error message to the output portion 46.

In the case where an instruction to display a 3D endoscope image on the monitor 5" has been issued with the 2D/3D change switch 15, the R image signal and the L image signal outputted from the endoscope 2 and subjected to various types of image processing are inputted from the 2D/3D switching portion 43 to the 3D processing portion 45'.

The structure and functions of the 3D processing portion 45' are similar to those of the 3D processing portion 55 of the monitor 5' according to the second embodiment, which has been described hereinbefore with reference to FIG. 8, except in that the output destination of the image signals, or the error message, is the output portion 46.

The output portion 46 outputs, to an input portion 51 of the monitor 5", the image signals inputted from the 2D processing portion 44' or the 3D processing portion 45'.

In the monitor 5", the image signals inputted to the input portion 51 are outputted to a video display portion 56, and 2D or 3D endoscope images are displayed.

As described hereinbefore, according to the present embodiment, even in the case where there is a fog on the objective lens or a stain has been attached to the objective lens, the 2D processing portion 44' and the 3D processing portion 45' are configured to selectively output the endoscope image of one of the eyes without a fog, generate a composite image without a fog by combining fog-free regions of the left-eye endoscope image and the right-eye endoscope image, or generate a pseudo-3D image using the composite image or the endoscope image of one of the eyes without a fog. Thus, a clear endoscope image can be outputted without the need to interrupt a manipulation.

In addition, according to the present embodiment, processes ranging from the detection of the foggy regions in the L image signals and the R image signals inputted from the endoscope 2 to the generation of the composite image in which the foggy region has been corrected are performed in the processor 4". Accordingly, the monitor 5" only has to display the image signals inputted from the processor 4" as they are, and therefore, a monitor capable of displaying 3D endoscope images and having a known configuration can be used as the monitor 5".

When any of the 3D endoscope apparatuses and the 3D video processing apparatuses according to embodiments of the disclosed technology is used, a clear endoscope image can be outputted without the need to interrupt a manipulation even in the case where there is a fog on either objective lens or a stain has been attached to either objective lens.

The various "portions" mentioned herein are conceptual elements corresponding to various functions of embodiments of the disclosed technology, and do not necessarily correspond to particular pieces of hardware or software routines in a one-to-one fashion. Accordingly, virtual circuit blocks, virtual circuit portions, having various functions of the embodiments have been assumed herein to describe the embodiments.

While several embodiments of the disclosed technology have been described hereinbefore, those embodiments have been presented by way of example only, and are not meant to limit the scope of the invention. These novel embodiments can be implemented in various other forms, and various omissions, substitutions, and changes may be made without departing from the gist of the invention. These embodiments and modifications thereof fall within the scope and gist of the invention, and within the scope of the invention recited in the appended claims and equivalents thereof.

In sum, one aspect of the disclosed technology is directed to a three-dimensional endoscope apparatus. The three-dimensional endoscope comprises a video signal input portion to which a first video signal is obtained by a first imaging system and a second video signal is obtained by a second imaging system are inputted. A video signal identification portion that identifies a two-dimensional video signal and a three-dimensional video signal are obtained from the video signal input portion. An image condition detection portion that, when the video signal identification portion has detected the two-dimensional video signal, analyzes a display area of a two-dimensional image to detect a foggy region therein. An image combining portion that, when the image condition detection portion has detected a foggy region in a video of at least one of the first imaging system and the second imaging system, combines both of the first video signal and the second video signal to generate a composite image in which fogginess of the foggy region being eliminated.

The three-dimensional endoscope apparatus further comprises a channel switch instruction portion that, when the image condition detection portion has detected a foggy region only in the video signal obtained from one of the first imaging system and the second imaging system, makes a switch to the other video signal. The three-dimensional endoscope apparatus further comprises a display portion that displays the two-dimensional video signal and the three-dimensional video signal. The foggy region is a region corresponding to at least one of a fog and/or a stain. The image condition detection portion divides each of a plurality of the two-dimensional images taken at intervals of a predetermined time into a plurality of regions, compares image information as to each of the divided regions between the plurality of two-dimensional images to calculate differences therebetween, counts the number of divided regions with respect to which the differences are zero, and determines that a foggy region has been detected in the two-dimensional images when the counted number of divided regions is equal to or greater than a first threshold value. The image information is red-green-blue pixel values. When the video signal identification portion has detected the three-dimensional video signal, the image condition detection portion analyzes a display area of a three-dimensional image to detect a foggy region therein. The three-dimensional endoscope apparatus further includes a pseudo-three-dimensional conversion portion that simulatively converts, to the three-dimensional video signal, a video signal without a foggy region obtained from one of the first imaging system and the second imaging system or the composite image generated by the image combining portion. The image condition detection portion divides each of a plurality of the three-dimensional images taken at intervals of a predetermined time into a plurality of regions, compares image information as to each of the divided regions between the plurality of three-dimensional images to calculate differences therebetween, counts the number of divided regions with respect to which the differences are zero, and determines that a foggy region has been detected in the three-dimensional images when the counted number of divided regions is equal to or greater than a first threshold value.

Another aspect of the disclosed technology is directed to a three-dimensional endoscope apparatus. Three-dimensional endoscope comprises a video signal input portion to which a first video signal is obtained by a first imaging system and a second video signal is obtained by a second imaging system are inputted. An image condition detection portion that analyzes a display area of a first image in the first video signal and/or a display area of a second image in the second video signal to detect a foggy region therein. An image combining portion that, when the image condition detection portion has detected a foggy region in a video of at least one of the first imaging system and the second imaging system, combines both of the first video signal and the second video signal to generate a composite image in which fogginess of the foggy region being reduced or eliminated. A pseudo-three-dimensional conversion portion that simulatively converts, to a three-dimensional video signal, a video signal without a foggy region obtained from one of the first imaging system and the second imaging system or the composite image generated by the image combining portion. A display portion that displays the three-dimensional video signal and a two-dimensional video signal formed by one of the first video signal, the second video signal, and the composite image.

The image condition detection portion divides each of a plurality of the first images taken at intervals of a predetermined time, or each of a plurality of the second images taken at intervals of a predetermined time, into a plurality of regions, compares image information as to each of the divided regions between the plurality of first images or between the plurality of second images to calculate differences therebetween, counts the number of divided regions with respect to which the differences are zero, and determines that a foggy region has been detected in the first images or the second images when the counted number of divided regions is equal to or greater than a first threshold value. The image information is red-green-blue pixel values.

A further aspect of the disclosed technology is directed to a three-dimensional video processing apparatus used in an endoscope system. The endoscope system comprises an endoscope having an elongated insertion portion and an operation portion being attached to one another. A lighting device, a display device and the three three-dimensional video processing apparatus all of which being attached to the endoscope to construct an image of a treatment target during operation. The three-dimensional video processing apparatus includes a video signal input portion to which a first video signal being obtained by a first imaging system and a second video signal being obtained by a second imaging system are inputted. An image condition detection portion that analyzes a display area of a first image in the first video signal and/or a display area of a second image in the second video signal to detect a foggy region therein. An image combining portion that, when the image condition detection portion has detected foggy regions in videos of both the first imaging system and the second imaging system, combines the first video signal and the second video signal to generate a composite image in which fogginess of the foggy regions being eliminated. An output portion that outputs a two-dimensional video signal formed by one of the first video signal, the second video signal, and the composite image.

The three-dimensional video processing apparatus further comprises a pseudo-three-dimensional conversion portion that simulatively converts, to a three-dimensional video signal, a video signal without a foggy region obtained from one of the first imaging system and the second imaging system or the composite image generated by the image combining portion. The output portion outputs the two-dimensional video signal or the three-dimensional video signal. The image condition detection portion divides each of a plurality of the first images taken at intervals of a predetermined time, or each of a plurality of the second images taken at intervals of a predetermined time, into a plurality of regions, compares image information as to each of the divided regions between the plurality of first images or between the plurality of second images to calculate differences therebetween, counts the number of divided regions with respect to which the differences are zero, and determines that a foggy region has been detected in the first images or the second images when the counted number of divided regions is equal to or greater than a first threshold value.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent.

Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. A three-dimensional endoscope apparatus comprising:
   a video signal input portion to which a first video signal being obtained by a first imaging system and a second video signal being obtained by a second imaging system are inputted;
   a video signal identification portion that identifies a two-dimensional video signal and a three-dimensional video signal obtained from the video signal input portion;
   an image condition detection portion that, when the video signal identification portion has detected the two-dimensional video signal, analyzes a display area of a two-dimensional image to detect a foggy region therein; and
   an image combining portion that, when the image condition detection portion has detected a foggy region in a video of at least one of the first imaging system and the second imaging system, combines both of the first video signal and the second video signal to generate a composite image in which fogginess of the foggy region being eliminated.

2. The three-dimensional endoscope apparatus of claim 1 further comprising:
   a channel switch instruction portion that, when the image condition detection portion has detected a foggy region only in the video signal obtained from one of the first imaging system and the second imaging system, makes a switch to the other video signal.

3. The three-dimensional endoscope apparatus of claim 2 further comprising:
   a display portion that displays the two-dimensional video signal and the three-dimensional video signal.

4. The three-dimensional endoscope apparatus of claim 1, wherein
   the foggy region is a region corresponding to at least one of a fog and/or a stain.

5. The three-dimensional endoscope apparatus of claim 1, wherein
   the image condition detection portion divides each of a plurality of the two-dimensional images taken at intervals of a predetermined time into a plurality of regions, compares image information as to each of the divided regions between the plurality of two-dimensional images to calculate differences therebetween, counts the number of divided regions with respect to which the differences are zero, and determines that a foggy region has been detected in the two-dimensional images when the counted number of divided regions is equal to or greater than a first threshold value.

6. The three-dimensional endoscope apparatus of claim 5, wherein
   the image information is red-green-blue pixel values.

7. The three-dimensional endoscope apparatus of claim 1, wherein,
   when the video signal identification portion has detected the three-dimensional video signal, the image condition detection portion analyzes a display area of a three-dimensional image to detect a foggy region therein; and the three-dimensional endoscope apparatus further includes a pseudo-three-dimensional conversion portion that simulatively converts, to the three-dimensional video signal, a video signal without a foggy region obtained from one of the first imaging system and the second imaging system or the composite image generated by the image combining portion.

8. The three-dimensional endoscope apparatus of claim 7, wherein the image condition detection portion divides each of a plurality of the three-dimensional images taken at intervals of a predetermined time into a plurality of regions, compares image information as to each of the divided regions between the plurality of three-dimensional images to calculate differences therebetween, counts the number of divided regions with respect to which the differences are zero, and determines that a foggy region has been detected in the three-dimensional images when the counted number of divided regions is equal to or greater than a first threshold value.

9. The three-dimensional endoscope apparatus of claim 8, wherein the image information is red-green-blue pixel values.

10. A three-dimensional endoscope apparatus comprising:

a video signal input portion to which a first video signal being obtained by a first imaging system and a second video signal being obtained by a second imaging system are inputted;

an image condition detection portion that analyzes a display area of a first image in the first video signal and/or a display area of a second image in the second video signal to detect a foggy region therein;

an image combining portion that, when the image condition detection portion has detected a foggy region in a video of at least one of the first imaging system and the second imaging system, combines both of the first video signal and the second video signal to generate a composite image in which fogginess of the foggy region being reduced or eliminated;

a pseudo-three-dimensional conversion portion that simulatively converts, to a three-dimensional video signal, a video signal without a foggy region obtained from one of the first imaging system and the second imaging system or the composite image generated by the image combining portion; and a display portion that displays the three-dimensional video signal and a two-dimensional video signal formed by one of the first video signal, the second video signal, and the composite image.

11. The three-dimensional endoscope apparatus of claim 10, wherein the image condition detection portion divides each of a plurality of the first images taken at intervals of a predetermined time, or each of a plurality of the second images taken at intervals of a predetermined time, into a plurality of regions, compares image information as to each of the divided regions between the plurality of first images or between the plurality of second images to calculate differences therebetween, counts the number of divided regions with respect to which the differences are zero, and determines that a foggy region has been detected in the first images or the second images when the counted number of divided regions is equal to or greater than a first threshold value.

12. The three-dimensional endoscope apparatus of claim 11, wherein the image information is red-green-blue pixel values.

13. A three-dimensional video processing apparatus used in an endoscope system, the endoscope system comprising:

an endoscope having an elongated insertion portion and an operation portion being attached to one another; and a lighting device, a display device and the three three-dimensional video processing apparatus all of which being attached to the endoscope to construct an image of a treatment target during operation and wherein the three-dimensional video processing apparatus includes a video signal input portion to which a first video signal obtained by a first imaging system and a second video signal obtained by a second imaging system are inputted, an image condition detection portion that analyzes a display area of a first image in the first video signal and/or a display area of a second image in the second video signal to detect a foggy region therein, an image combining portion that, when the image condition detection portion has detected foggy regions in videos of both the first imaging system and the second imaging system, combines the first video signal and the second video signal to generate a composite image in which fogginess of the foggy regions being eliminated, and an output portion that outputs a two-dimensional video signal formed by one of the first video signal, the second video signal, and the composite image.

14. The three-dimensional video processing apparatus of claim 13, further comprising:

a pseudo-three-dimensional conversion portion that simulatively converts, to a three-dimensional video signal, a video signal without a foggy region obtained from one of the first imaging system and the second imaging system or the composite image generated by the image combining portion, wherein the output portion outputs the two-dimensional video signal or the three-dimensional video signal.

15. The three-dimensional video processing apparatus of claim 13, wherein the image condition detection portion divides each of a plurality of the first images taken at intervals of a predetermined time, or each of a plurality of the second images taken at intervals of a predetermined time, into a plurality of regions, compares image information as to each of the divided regions between the plurality of first images or between the plurality of second images to calculate differences therebetween, counts the number of divided regions with respect to which the differences are zero, and determines that a foggy region has been detected in the first images or the second images when the counted number of divided regions is equal to or greater than a first threshold value.

16. The three-dimensional video processing apparatus of claim 15, wherein the image information is red-green-blue pixel values.

* * * * *